United States Patent [19]
Wright

[11] Patent Number: 5,646,155
[45] Date of Patent: Jul. 8, 1997

[54] DRUGS TO PREVENT RECURRENT HERPES VIRUS INFECTIONS

[75] Inventor: George E. Wright, Worcester, Mass.

[73] Assignee: University of Massachusetts Medical Center, Worcester, Mass.

[21] Appl. No.: 365,769

[22] Filed: Dec. 29, 1994

Related U.S. Application Data

[63] Continuation-in-part of Ser. No. 241,686, May 12, 1994, abandoned.

[51] Int. Cl.$^6$ .................. A61K 31/52; C07D 473/32; C07D 473/18; C07D 473/16
[52] U.S. Cl. .................. 514/261; 514/262; 514/266; 544/276; 544/277
[58] Field of Search .................. 544/276, 277; 514/261, 262, 266

[56] References Cited

U.S. PATENT DOCUMENTS 4,663,446  5/1987  Wright .................. 536/28

OTHER PUBLICATIONS

Kazimierczuk, J. Med. Chem 33, 1683 (1990).
F. Focher, et al., A Novel Pharmacological Approach to Herpes Virus Infections; J. of Chemotherapy—Supplement n.4—1989, pp. 1107–1108.
F. Focher, et al., Nucleoside Analogs As Non–Substrate Inhibitors of Herpes Simplex Viruses Thymidine Kinase; Meth. and Find Exp. Clin. Pharmacol. 11:577–82, 1989.
F. Focher, et al., N$^2$–Substituted Guanine Derivatives Act As Selective Non Substrate Inhibitors Of HSV I Thymidine Kinase; Biochemical Pharmacology, 37:1877–78; 1988.
J. Gambino, et al., Quantitative Structure–Activity Relationships of N$^2$–Phenylguanines As Inhibitors Of Herpes Simplex Virus Thymidine Kinases; J. Med. Chem. 35:2979–83, 1992.
N. Bourne, et al., Assessment Of A Selective Inhibitor Of HSV Thymidine Kinase (L–653,180) As Therapy For Experimental Recurrent Genital Herpes; Antimicrobial Agents and Chemotherapy, 36:2020–24, 1992.
F. Focher, et al., N$^2$–Phenyldeoxyguanosine: A Novel Selective Inhibitor Of Herpes Simplex Thymidine Kinase; J. Med. Chem. 31:1496–1500, 1988.
C. Hildebrand, et al., Structure–Activity Relationships of N$^2$–Substituted Guanines As Inhibitors Of HSV1 and HSV2 Thymidine Kinases; J. Med. Chem. 33:203–06, 1990.
H.E. Kaufman, et al., Suppression Of Ocular Herpes Recurrences By A Thymidine Kinase Inhibitor In Squirrel Monkeys; Antiviral Res., 16 (1991), pp. 227–232.

D.A. Leib, et al., Specific Inhibitors Of HSV Thymidine Kinase Diminish Reactivation Of Latent Virus From Explanted Murine Ganglia, Antimicrobial Agents and Chemotherapy; 34:1285–86, 1990.

S. Spadari and G. Wright, Antivirals Based On Inhibition Of Herpesvirus Thymidine Kinases; Drugs, News & Perspectives 2:333–36, 1989.

Harnden et al., Analogues of the Antiviral Acyclonucleoside 9–(4–Hydroxy–3–hydroxymethylbutyl)guanine, Pt. 4, Substitution on the 2–Amino Group; J. Chem. Soc. Perkin Trans. I:2207–2213, 1989.

Wright, Herpesivrus Thymidine Kinase Inhibitors, International Antiviral News, 2(6):84–86, 1994.

Xu et al., Synthesis, Properties, and Pharmacokinetic Studies of N$^2$–Phenylguanine Derivatives as Inhibitors of Herpes Simplex Virus Thymidine Kinases, Journal of Medicinal Chemistry 38(1):49–57, 1995.

*Primary Examiner*—Mark L. Berch
*Attorney, Agent, or Firm*—Fish & Richardson P.C.

[57] ABSTRACT

N$^2$–substituted alkylguanine and N$^2$–substituted phenylguanine compounds which prevent recurrent herpes simplex infections are disclosed. By virtue of their ability to inhibit herpes virus thymidine kinase in vivo, such compounds will prevent, reduce the frequency of, or reduce the severity of recurring HSV infections in humans. The N$^2$–alkylguanine compounds are of the formula:

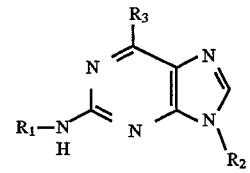

where $R_1$ is a normal or branched chain $C_nH_{2n+1}$ (where n is 1–12); $R_2$ is H, 2-deoxyribofuranosyl, $(CH_2)_nOH$ (where n is 2–5), $CH_2CH(OH)CH_2OH$, $(CH_2)_n$—COOH (where n is 1–4), $CH_2CH(OH)CH_2$—O—$COR_4$, $(CH_2)_n$—O—$COR_4$ (where n is 2–5), or $(CH_2)_nCO$—$OR_4$ (where n is 1–4); $R_4$ is $CH_3$, $CH_2CH_3$, $CH_2CH_2NH_2$, $CH_2CH_2N(C_2H_5)_2$ or $CH_2CH_2CO_2H$; and $R_3$ is OH, H, Cl or $NH_2$, or a tautomer or a pharmaceutically acceptable salt thereof. The N$^2$–substituted phenylguanine compounds are of similar structure, where $R_1$ is a phenyl or a phenyl substituted at the 3 and 4 positions with an H, a hydrophobic or electron extracting group, or a $CH_2CH_3$.

30 Claims, 4 Drawing Sheets

1

DRUGS TO PREVENT RECURRENT HERPES VIRUS INFECTIONS

This application is a continuation-in-part of U.S. Ser. No. 08/241,686, filed May 12, 1994, ABN in the United States Patent and Trademark Office.

BACKGROUND OF THE INVENTION

The invention relates to therapies for herpes virus infections in mammals.

Herpes Simplex 1 (HSV1), Herpes Simplex 2 (HSV2), Varicella-Zoster virus (VZV), and Epstein Barr virus (EBV) infections in humans are characterized by episodes of epithelial eruptions involving active virus production alternating with periods without clinical symptoms, i.e., in which the virus is in a latent state.

In the case of the herpes virus VZV, the initial acute infection is known as chicken pox, and reactivation from the subsequent latent infection is manifested as the disease shingles. Animal models of the latent state show that at some defined period following inoculation with virus, conventional homogenization techniques are unable to detect free virus, but that the presence of the viral genome can be demonstrated by explanation rescue (cocultivation) techniques (Price, Cancer Invest. 1985, 3:285–92, 389–403). In the mouse latency model for HSV1, viral genomes can be detected in sensory ganglia, most abundantly in trigeminal ganglia. The stimuli that cause virus to travel to neural cell bodies, the form of the viral genome present in the cells, and the molecular events that occur during reactivation of the virus are not known.

Development of antiherpetic drugs has focused on targeting inhibitors against the various enzymes encoded by the herpes viruses. Among virus-specific enzymes, the viral DNA polymerase has been an important target for nucleoside analogs such as acyclovir, bromovinyldeoxyuridine and DHPG.

HSVI, HSV2, VZV, and EBV are known to encode a thymidine kinase ("TK") enzyme in addition to the viral DNA polymerase. While the viral DNA polymerase is known to catalyze the replication of the viral genome, the role(s) of the viral TKs are not well understood. The herpes virus TKs share homologies at the gene and amino acid sequence levels (summarized by Folkers et al., J. Computer-Aided Molec. Design, 5, 385–404 (1991)), and have common, though not identical, enzymatic properties. TK is not present simply to increase the pool of thymidine phosphates for viral DNA synthesis; mutant HSV1 strains deficient in TK activity replicate well in cell cultures and produce active infections in animals. Observations that TK⁻ HSV mutants cannot produce latent, reactivatable infections in animals have led to the hypothesis that TK expression is required for the establishment or reactivation of virus from its latent state, particularly in tissues such as peripheral nerve ganglia where host TK expression and DNA synthesis are absent (Price, R. W. Cancer Invest. 1985, 3:285–92, 389–403).

Two major groups of TK inhibitors have been developed as potential herpesvirus therapeutics. The first are analogs of the substrate thymidine, involving modifications at the 5-position of the pyrimidine ring and/or the 5'-OH group of the sugar ring. The second group consists of guanine base and nucleoside analogs, including several 9-cycloalkylmethyl guanines in which TK inhibition and substrate properties have been separated, and a series of nonsubstrate derivatives with substituents on the exocyclic amino group of guanine.

SUMMARY OF THE INVENTION

In a first aspect, the invention features 9-substituted $N^2$-phenylguanines of the formula:

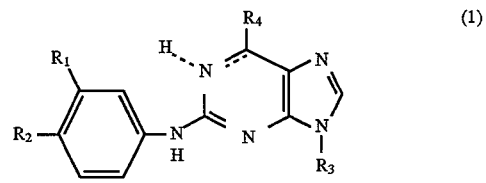

where each $R_1$ and $R_2$, independently,=H or a hydrophobic, electron-attracting substituent or $CH_2CH_3$; and $R_3=$

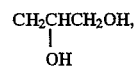

$(CH_2)_nOH$ (where n is 2–5), $(CH_2)_nCOOH$ (where n is 1–4),

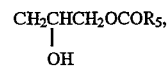

$(CH_2)_nOCOR_5$ (where n is 2–5), or $(CH_2)_nCOOR_5$ (where n is 1–4 and $R_5=CH_3$, $CH_2CH_3$, $CH_2CH_2NH_2$, $CH_2CH_2N(C_2H_5)_2$, or $CH_2CH_2CO_2H$); and $R_4=O$, H, Cl, or $NH_2$.

A hydrophobic, electron-attracting substituent is defined as any substituent which has both a positive π constant and a positive σ constant. Examples, of suitable such groups are H, X, $CX_3$, $CX_2CX_3$, $CH_2CX_3$, $CHX_2$, or $OCX_3$ (where X=a halogen, preferably fluorine).

Preferred $N^2$-phenylguanine compounds which are a part of the first aspect of the invention have the formulae:

A) 9-(2,3-dihydroxypropyl)-$N^2$-phenylguanines (DHBPG) where in formula (1), above, each $R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);

$R_3=$

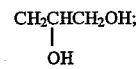

and
$R_4=O$.

B) 9-(ω-hydroxyalkyl)-$N^2$-phenylguanines where, in formula (1), above, each $R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);
$R_3=(CH_2)nOH$ (where n is 2–5); and
$R_4=O$.

C) 9-(ω-carboxyalkyl)-$N^2$-phenylguanines where, in formula (1), above, each
$R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);
$R_3=(CH_2)_nCOOH$, where n=1–4; and
$R_4=O$.

D) Compounds of formula (1), above, where each
$R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);

$R_3=CH_2OHCHCH_2OCOR_5$, $(CH_2)_nOCOR_5$ (where n=2–5), or $(CH_2)_nCOOR_5$ (where n=1–4); and
$R_5=CH_3$, $CH_2CH_3$, $CH_2CH_2NH_2$, $CH_2CH_2N(C_2H_5)_2$, or $CH_2CH_2CO_2H$; and
$R_4=O$.

E) 6-substituted purine compounds of formula (1) where the $R_1$, $R_2$, and $R_3$ groups are those described in A–D, above, and where
$R_4=H$, Cl, or $NH_2$.

F) Acid and base salts of the compounds of classes A–E, such as hydrochloride, sulfate, or phosphate salts of basic compounds, and sodium, potassium, or calcium salts of acidic compounds.

G) The most preferred $N^2$-Phenylguanine compounds of the first aspect of the invention are:
a) 9-(2,3-Dihydroxypropyl)-$N^2$-phenylguanine [DHBPG],
b) 9-(2,3-Dihydroxypropyl)-$N^2$-(m-[trifluoromethyl] phenyl)guanine,
c) 9-(2,3-Dihydroxypropyl)-$N^2$-(p-bromophenyl) guanine,
d) 9-(2-Hydroxyethyl)-$N^2$-phenylguanine [HE-PG],
e) 9-(2-Hydroxyethyl)-$N^2$-(m-[trifluoromethyl]phenyl) guanine,
f) 9-(2-Hydroxyethyl)-$N^2$-(p-bromophenyl)guanine,
g) 9-(4-Hydroxybutyl)-$N^2$-phenylguanine [HB-PG],
h) 9-(4-Hydroxybutyl)-$N^2$-(m-[trifluoromethyl]phenyl) guanine,
i) 9-(4-Hydroxybutyl)-$N^2$-(p-bromophenyl)guanine,
j) ($N^2$-Phenylguan-9-yl)acetic acid [PG-AA],
k) ($N^2$-[m-[Trifluoromethyl]phenyl]guan-9-yl)acetic acid,
l) ($N^2$-(p-bromophenyl) guan-9-yl)acetic acid,
m) 9-(2-Hydroxy-3-acetoxypropyl)-$N^2$-phenylguanine,
n) 9-(2-Hydroxy-3-acetoxypropyl) -$N^2$-(m-[trifluoromethyl]phenyl)guanine,
o) 9-(2-Hydroxy-3-acetoxypropyl)-$N^2$-(p-bromophenyl)guanine,
p) 9-(2-Acetoxyethyl)-$N^2$-phenylguanine,
q) 9-(2-Acetoxyethyl)-$N^2$-(m-[trifluoromethyl]phenyl) guanine, and
r) 9-(2-Acetoxyethyl)-$N^2$-(p-bromophenyl)guanine.

In the second aspect, the invention features $N^2$-phenylguanines of the formula:

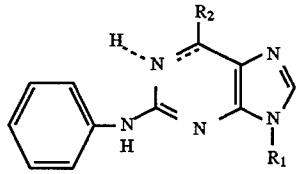

wherein $R_1$=2-deoxyribofuranosyl, $(CH_2)_n$ OH (where n is 2–5), $CH_2CHOHCH_2OH$, $(CH_2)_n$—COOH (where n is 1–4),

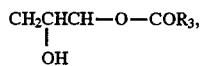

$(CH_2)_n$—O—$COR_3$ (where n is 2–5), or $(CH_2)_nCO$—$OR_3$ (where n is 1–4)
wherein $R_3=CH_3$, $CH_2CH_3$, $CH_2CH_2NH_2$, $CH_2CH_2N(C_2H_5)_2$, or $CH_2CH_2CO_2H$; and
$R_2=O$, H, Cl or $NH_2$, wherein when $R_1$ is 2-deoxyribofuranosyl $R_2$ is not O.

In a third aspect, the invention features $N^2$-alkylguanines of the formula

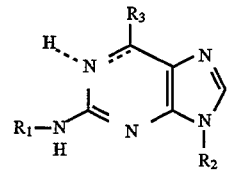

wherein
$R_1=C_nH_{2n+1}$ or isomeres thereof (where n is 1–12);
$R_2$=H, 2-deoxyribofuranosyl, $(CH_2)_nOH$ (where n is 2–5), $CH_2CHOHCH_2OH$, $(CH_2)_n$—COOH (where n is 1–4), $CH_2CHOHCH_2$—O—$COR_4$, $(CH_2)_n$—O—$COR_4$ (where n is 2–5), or $(CH_2)_nCO$—$OR_4$ (where n is 1–4); wherein
$R_4=CH_3$, $CH_2CH_3$, $CH_2CH_2NH_2$, $CH_2CH_2N(C_2H_5)_2$, or $CH_2CH_2CO_2H$; and
$R_3$=O,H,Cl or $NH_2$.

Acid and base salts of all of the above compounds are also a part of the invention.

Preferred alkyl guanines of the invention are as follows:
a) 9-(2-deoxyribofuranosyl)-$N^2$-methylguanine [MedG];
b) 9-(2-deoxyribofuranosyl)-$N^2$-ethylguanine [EtdG];
c) 9-(2-deoxyribofuranosyl)-$N^2$-n-propylguanine [PrdG];
d) 9-(2-deoxyribofuranosyl)-$N^2$-n-dodecylguanine [$C_{10}$dG];
e) 9-(2,3-Dihydroxypropyl)-$N^2$-propylguanine [DHP-PrG];
f) 9-(2,3-Dihydroxypropyl)-$N^2$-n-dodecylguanine [DHP-$C_{10}$G];
g) 9-(2-Hydroxyethyl)-$N^2$-propylguanine [HE-PrG];
h) 9-(2-Hydroxyethyl)-$N^2$-n-dodecylguanine [HE-$C_{10}$G];
i) 9-(4-Hydroxybutyl)-$N^2$-proplyguanine [HB-PrG];
j) 9-(4-Hydroxybutyl)-$N^2$-n-dodecylguanine [HB$C_{10}$G];
k) $N^2$-(n-Dodecyl)guanine [$C_{12}$G];
l) $N^2$-(n-Decyl)guanine [$C_{10}$G];

Furthermore, it is noted that the 6-H purine present in some of the above compounds may be converted in vivo by xanthine oxidase to give the corresponding 6-oxo(guanine) derivatives, which are biologically active compounds of the invention. Conversion of the 6-Cl or 6-$NH_2$ group by adenosine deaminase in vivo will give the active 6-oxo (guanine) derivatives.

In a related aspect of the invention, methods are provided for using the compounds of the invention for the treatment of herpes virus infections in human patients when the infecting virus encodes a thymidine kinase. For example, HSV1, HSV2, VZV, and EBV viral infections causing diseases such as oral herpes, genital herpes, encephalitis, and shingles may be treated.

The compounds are particularly useful for preventing viral reactivation in individuals infected with HSV1, HSV2 and VZV. Preferred compounds for treating HSV1 and HSV2 infection are the $N^2$-phenylguanine compounds described is the first aspect of the invention. More preferred compounds for use in methods of treating HSV1 and HSV2 infection are those described as "preferred $N^2$-phenylguanine compounds" in the first aspect of the invention. Most preferred compounds for use in methods of treating HSV1 and HSV2 infection are
a) 9-(2,3-Dihydroxypropyl)-$N^2$-phenylguanine [DHBPG];
b) 9-(2,3 -Dihydroxypropyl)-$N^2$-(m-[trifluoromethyl] phenyl)guanine;
c) 9-(2,3-Dihydroxypropyl)-$N^2$-(p-bromophenyl)guanine;
d) 9-(2-Hydroxyethyl)-$N^2$-phenylguanine [HE-PG];
e) 9-(2-Hydroxyethyl)-$N^2$-(m-[trifluoromethyl]phenyl) guanine;

f) 9-(2-Hydroxyethyl)-$N^2$-(p-bromophenyl)guanine;
g) 9-(4-Hydroxybutyl)-$N^2$-phenylguanine [HB-PG];
h) 9-(4-Hydroxybutyl)-$N^2$-(m-[trifluoromethyl]phenyl) guanine;
i) 9-(4-Hydroxybutyl)-$N^2$-(p-bromophenyl)guanine;
j) ($N^2$-Phenylguan-9-yl)acetic acid [PG-AA];
k) ($N^2$-[m-[Trifluoromethyl]phenyl]guan-9-yl)acetic acid;
l) ($N^2$-(p-bromophenyl) guan-9-yl)acetic acid;
m) 9-(2-Hydroxy-3-acetoxypropyl)-$N^2$-phenylguanine;
n) 9-(2-Hydroxy-3-acetoxypropyl)-$N^2$-(m-[trifluoromethyl]phenyl)guanine;
o) 9-(2-Hydroxy-3-acetoxypropyl)-$N^2$-(p-bromophenyl) guanine;
p) 9-(2-Acetoxyethyl)-$N^2$-phenylguanine;
q) 9-(2-Acetoxyethyl)-$N^2$-(m-[trifluoromethyl]phenyl) guanine; and
r) 9-(2-Acetoxyethyl)-$N^2$-(p-bromophenyl)guanine.

Preferred compounds for treating VZV infection are the phenylguanine compounds of the second aspect of the invention and the alkylguanine compounds of the third aspect of the invention. Most preferred compounds for treating VZV are:

a) 9-(2-deoxyribofuranosyl)-$N^2$-methylguanine [MedG];
b) 9-(2-deoxyribofuranosyl)-$N^2$-ethylguanine [EtdG];
c) 9-(2-deoxyribofuranosyl)-$N^2$-n-propylguanine [PrdG];
d) 9-(2-deoxyribofuranosyl)-$N^2$-n-dodecylguanine [$C_{10}$dG];
e) 9-(2,3-Dihydroxypropyl)-$N^2$-propylguanine [DHP-PrG];
f) 9-(2,3-Dihydroxypropyl)-$N^2$-n-dodecylguanine [DHP-$C_{10}$G];
g) 9-(2-Hydroxyethyl)-$N^2$-propylguanine [HE-PrG];
h) 9-(2-Hydroxyethyl)-$N^2$-n-dodecylguanine [HE-$C_{10}$G];
i) 9-(4-Hydroxybutyl)-$N^2$-propylguanine [HB-PrG];
j) 9-(4-Hydroxybutyl)-$N^2$-n-dodecylguanine [HB$C_{10}$G];
k) $N^2$-(n-Dodecyl)guanine [$C_{12}$G];
l) $N^2$-(n-Decyl)guanine [$C_{10}$G]; and
m) 9-(2-Deoxyriboduranosyl)-$N^2$-phenylguanine [PhdG].

Acid and base salts of the compounds may also be used in the methods of the invention.

The compounds of the invention may be used to prevent or reduce the severity of recurrent infections, including infections in non-replicating tissues.

Other features and advantages of the invention will be apparent from the following detailed description, and from the claims.

BRIEF DESCRIPTION OF THE DRAWINGS

FIG. 1 shows the time course for interperitoneal (i.p.) and intravenous (i.v.) administration of HB-PG in 90% DMSO, 33% DMSO and corn oil.

FIG. 2 shows the time course for HB-PG when administered in a corn oil suspension by i.v. and i.p. injection to rabbits.

FIG. 3 shows the time course for plasma concentration of HB-PG when administered to squirrel monkeys when administered by i.p. injection.

FIG. 4 shows the time course for HB-PG administration to squirrel monkeys when administered by i.v. injection.

DETAILED DESCRIPTION

I. 9-substituted-$N^2$-phenylguanine Compounds

Figure 1:
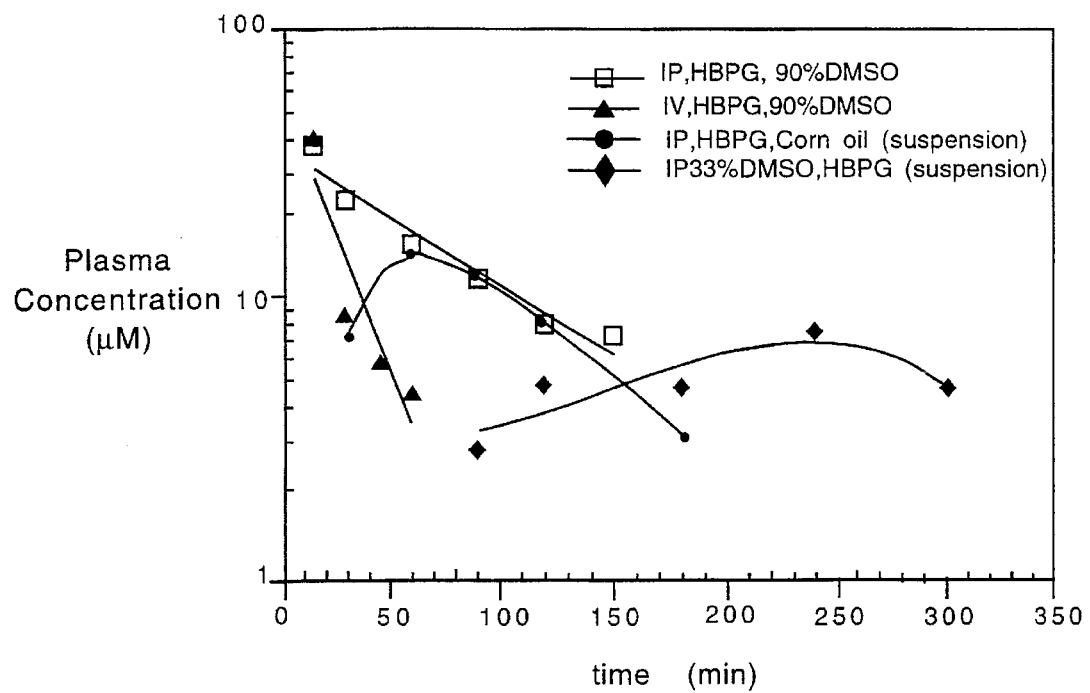
FIGS. 1-4 show the plasma concentration time curves for HB-PG.

By virtue of their ability to inhibit herpes virus thymidine kinases in vivo, the 9-substituted $N^2$-phenylguanines described herein will prevent, reduce the frequency of, or reduce the severity of recurrent herpes virus infections in humans. In addition, such compounds can reduce the virulence of HSV infections in non-replicating tissues, including tissues affected during HSV encephalitis.

A. DHP-PG Compounds

Some of the compounds of the invention contain a dihydroxypropyl group, which increases water solubility, and a meta-phenyl substituent, which we have found increases potency. These compounds are:

9-(2,3-dihydroxypropyl)-$N^2$-phenylguanines (DHP-PG), of formula (1), wherein
    each $R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);
    $R_3$=

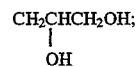

and
    $R_4$=O.

B. ω-hydroxyalkyl and ω-carboxyalkyl Containing Compounds

Some of the compounds of the invention have a ω-hydroxyalkyl group, which increases water solubility, and a meta-phenyl substituent. This combination of groups increases potency.

Another class of compounds are those including a ω-carboxyalkyl group in combination with a suitable metaphenyl substituent. Like the ω-hydroxyalkyl group, the ω-carboxyalkyl group increases water solubility.

These compounds are:

i) 9-(ω-Hydroxyalkyl)-$N^2$-phenylguanines wherein
    each $R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);
    $R_3$=$(CH_2)_n OH$, where n=2-5; and
    $R_4$=O; and ii) 9-(ω-carboxyalkyl)-$N^2$-phenylguanines wherein
    each of $R_1$ and $R_2$, independently,=H, $CH_2CH_3$, X, $CX_3$, $CX_2CX_3$, $CH_2CX_3$, $CHX_2$, or $OCX_3$ (where X=a halogen, preferably fluorine);
    $R_3$=$(CH_2)_n CO_2H$ (where n=1-4); and
    $R_4$=O.

C. Additional $N^2$-phenylguanine Compounds.

$N^2$-phenylguanines of the general formula:

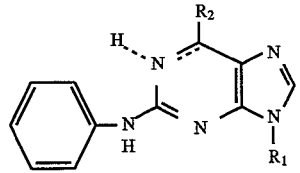

wherein $R_1$=2-deoxyribofuranosyl, $(CH_2)_n OH$ (where n is 2-5), $CH_2CHOHCH_2OH$, $(CH_2)_n$—COOH (where n is 1-4),

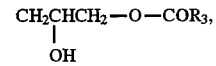

—O—$COR_3$, $(CH_2)_n$—O—$COR_3$(where n is 2-5), or $(CH_2)_n CO$—$OR_3$ (where n is 1-4);
wherein $R_3$=$CH_3$, $CH_2CH_3$, $CH_2CH_2NH_2$, $CH_2CH_2N(C_2H_5)_2$, or $CH_2CH_2CO_2H$; and wherein $R_2$=O, H, Cl or $NH_2$ have been found to be useful for inhibiting the thymidine kinase in herpes viruses. The inhibitor has the effect of reducing the reactivation following viral latency.

D. Useful Modifications of the $N^2$-phenylguanine Compounds

Any of The compounds of the invention may be modified in a number of ways to increase both the effectiveness of drug delivery and activity of the compounds as thymidine kinase inhibitors. In addition, acid or base salts of the compounds may be utilized.

The invention also provides compounds which are precursors of the active compounds stated above. For example, precursor compounds which are esters of the above compounds will be cleaved by non-specific plasma esterases in vivo to release active compounds. The $N^2$-phenylguanine compounds may include the following modifications:

esters where $R_1$, $R_2$ and $R_3$ are as follows:

$R_1$, $R_2$=H, $CH_2CH_3$, $CF_3$, $CF_2CF_3$, $CH_2CF_3$, $CHF_2$, $OCF_3$, or a halogen;

$R_3$=

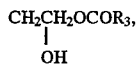

$(CH_2)_nOCOR_3$ (where n=2–5), or $(CH_2)_nCOOR_5$ (where n=1–4);

$R_5$=$CH_3$, $CH_2CH_3$, $CH_2CH_2NH_2$, $CH_2CH_2N(C_2H_5)_2$, or $CH_2CH_2CO_2H$; and $R_4$=oxygen.

Another class of precursor compounds include the 6-substituted purine analogs of the compounds given above in A–C, where $R_4$=H, Cl, or $NH_2$. Conversion of the 6-H purine in these $R_4$ substitutions by xanthine oxidase in vivo will give the corresponding 6-oxo (guanine) derivative, which is an active compound. Reaction of the 6-Cl or 6-$NH_2$ group with adenosine deaminase in vivo will give the 6-oxo (guanine) derivatives which are also active compounds.

II. $N^2$-alkylquanine Compounds

In a second aspect, the invention features $N^2$-alkylguanines of the formula

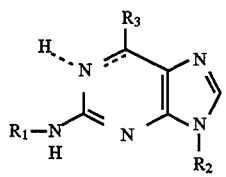

wherein $R_1$=$C_nH_{2n+1}$ or isomeres thereof (where n is 1–12);

$R_2$=H, 2-deoxyribofuranosyl, $(CH_2)_n$ OH (where n is 2–5), $CH_2CHOHCH_2OH$, $(CH_2)_n$—COOH (where n is 1–4), $CH_2CHOHCH_2$—O—$COR_4$, $(CH_2)_n$—O—$COR_4$ (where n is 2–5), or $(CH_2)_nCO$—$OR_4$ (where n is 1–4); wherein $R_4$=$CH_3$, $CH_2CH_3$, $CH_2CH_2NH_2$, $CH_2CH_2N(C_2H_5)2$, or $CH_2CH_2CO_2H$; and $R_3$=O,H,Cl or $NH_2$ have been found to be useful for inhibiting the thymidine kinase in herpes viruses. The inhibitor has the effect of reducing the reactivation following viral latency.

Acid and base salts of these compounds are also a part of the invention and may also be utilized as described herein.

It may be noted that where there is a 6-H purine present in some of the above compounds the 6-H purine may be converted in vivo by xanothine oxidase to give the corresponding 6-oxo(guanine) derivatives, which are biologically active compounds of the invention. Conversion of the 6-Cl or 6-$NH_2$ group by adenosine deaminase in vivo will also give the active 6-oxo(guanine) derivatives.

III. Methods for the screening of compounds in vitro and in vivo

A. Murine in vitro explant-cocultivation model for HSV1.

Screening of compounds is carried out using an in vitro explant cocultivation model in mice. Ocular HSV1 infections are initiated and, after subsidence of the infectious phase (several days), latent HSV1 infection becomes established in the trigeminal ganglia of the mice. The ganglia are then surgically removed and minced or homogenized, and this explanted tissue is cocultivated on mammalian cells, typically Vero cells. The frequency of reactivation is determined as the percentage of ganglia that produce HSV1 virus (as measured by viral cytopathic effect (CPE)) in the cultures. Effective drugs present during the cocultivation period will decrease the frequency of reactivation relative to untreated cocultures. See Leib et al. (J. Virol. 63:759–768 (1989)), incorporated herein by reference, and statements herein for further experimental details.

B. Murine eye model for HSV1.

About 40–50 days after establishment of latent HSV1 infection (as described above) mice are treated with cyclophosphamide, dexamethasone and ultraviolet irradiation to induce viral reactivation. Eyewashings are taken for inoculation of cultured mammalian cells, typically Vero cells, and viral induced CPE is measured. Drugs present during the latency or reactivation phase may decrease the number of animals from which virus can be recovered, or delay the time at which virus appears in the eyewashings. See, Shimeld et al., J. Gen. Virol. 71:397–404 (1990), incorporated herein by reference, for additional experimental detail.

C. Murine ear model for HSV1.

After initiation of HSV1 infection of the ears of mice, latent infection becomes established in cervical ganglia. After 3–5 weeks cellophane tape is applied and removed from the ears of mice to induce viral reactivation. Erythema of the ear surface is evidence of reactivation. Drugs present before and/or during the reactivation stimulus may decrease the degree of erythema or delay its onset, and may decrease the yield of virus from explant-cocultivation assays of cervical ganglia. For further experimental methods see, Hill et al., J. Gen. Virol. 39:21–28 (1978), incorporated herein by reference.

D. Rabbit and squirrel monkey eye models for HSV1.

Several weeks after establishment of latent HSV1 infection in the rabbit eye, sterile deionized water is injected intrastromally to induce reproducible, high frequency reactivation of virus within 48–72 hours. Drug treatment will decrease the numbers of eyes shedding virus, as measured by viral CPE caused by inoculation of cultured mammalian cells with eyewashings, and/or may delay the onset of virus reactivation. See, Gordon et al., Invest. Ophthalmol. Vis. Sci. 31:921–924 (1990), incorporated herein by reference, for additional experimental detail. An analogous model has been documented in the squirrel monkey, but reactivation occurs spontaneously 25 days or longer after initial infection. See, Varnell et al., Curr. Eye Res. 6:277–279 (1987); Kaufman et al., Antiviral Res. 16:227–232 (1991), all incorporated herein by reference.

E. Guinea pig vaginal model for HSV2.

Latent infections of HSV2 become established in dorsal sympathetic ganglia of guinea pigs after vaginal membrane infection. After 48 days animals are observed for recurrent vaginal lesions. Drugs present during the latent phase may decrease the frequency or severity of lesions and/or delay the onset of viral lesions. See, Stanberry et al., J. Infect. Dis. 146:397–404; Bourne et al., Antimicr. Agents Chemother. 36:2020–2024 (1992), all incorporated herein by reference, for additional experimental detail.

F. Guinea pig model of VZV latency.

The most useful animal models of VZV infections or latency involve VZV infection of the cornea of guinea pigs. Guinea pigs are innoculated to cause acute keratitis and the establishment of short term latency in trigeminal ganglia (Pavan-Langston, D. and Dunkel, E. C. (1989) Arch. Ophthalmol. 107, 1068–1072). Latent VZV can be recovered by whole cell coculture from the ganglia 5–11 days following inoculation.

IV. Therapeutic Administration of Compounds

The compounds of the invention are formulated for pharmaceutical or veterinary use, optionally together with an acceptable diluent, carrier or excipient and/or in unit dosage form. In using the compounds of the invention, conventional pharmaceutical or veterinary practice may be employed to provide suitable formulations or compositions.

Thus, the formulations of this invention can be administered by parenteral administration, for example, intravenous, subcutaneous, intramuscular, intraorbital, opthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the use of surgical implants which release the compounds of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations can be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The compounds of the invention can be used as the sole active agents, or can be used in combination with other active ingredients, e.g., direct antiviral drugs, growth factors which could facilitate neuronal survival in neurological diseases, or peptidase or protease inhibitors.

The concentration of the compound in the formulations of the invention will vary depending upon a number of factors, including the dosage to be administered, and the route of administration.

In general terms, the compounds of the invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the herpes infection being addressed, the overall health of the patient, and the route of administration. For topical and oral administration, formulations and dosages can be similar to those used for other anti-herpes drugs, e.g., acyclovir.

IV. Examples

The following examples are provided to illustrate the invention, not to limit it.

EXAMPLE 1

Synthesis of 9-substituted-$N^2$-phenylquanines
General.

NMR spectra were determined on a Varian Unity 300 instrument. Spectra were obtained in $Me_2SO$-$d_6$ solution with TMS as internal reference for $^1H$ spectra and $CFCl_3$ as internal reference for $^{19}F$ spectra. UV spectra were obtained on a Gilford Response spectrophotometer.

9-(2,3-Dihydroxypropyl)-$N^2$-phenylguanine [DHP-PG].

a. Sodium hydride (161 mg, 4 mmol; 60% suspension in mineral oil) was added to a suspension of 2-anilino-6-chloropurine (1 g, 4 mmol; Focher et al. (1988) J. Med. Chem. 31:1496–1500) in anhydrous acetonitrile (240 ml) at room temperature. After stirring for 1 hr epibromohydrin (0.35 ml, 4 mmol) was added, and the suspension was stirred for 48 hr. An equal volume of chloroform was added, and, after filtration through Celite, the filtrate was evaporated to dryness. The residue was chromatographed on silica gel, and the major product was eluted with chloroform to give 417 mg (34% yield) of 2-anilino-6-chloro-9-(2,3-epoxypropyl)purine. 1H NMR δ9.97 (s, 2-NH), 8.24 (s, 8-H), 7.40 (m, $C_6H_5$), 4.38 (m, 1'-$CH_2$), 3.45 (m, 2'-CH), 2.72 (m, 3'-$CH_2$). Further elution gave 46 mg (3.8% yield) of the minor 7-isomer.

b. A suspension of the 9-isomer from above (60 mg) in 0.5N sodium hydroxide solution (24 ml) was heated at reflux for 2 hr. After neutralization with 0.5N hydrochloric acid, the solution was placed in the refrigerator overnight. The colorless solid was collected and washed with water to give 37 mg (62%) of 9-(2,3-dihydroxypropyl)-$N^2$-phenylguanine. Colorless crystals were obtained after crystallization from DMF/chloroform, mp 342°–344° C. $^1H$ NMR δ10.49 (s, 1-H), 8.81 (s, 2-NH), 7.73 (s, 8-H), 7.35 (m, $C_6H_5$), 5.07 (d, 2'-OH), 4.77 (t, 3'-OH), 4.05 (m, 1'-H) 3.88 (m, 2'-H), 3.33 (m, 3'-H), UV $\lambda_{max}$ ($H_2O$) 275.5 nm (ε19200), (1-octanol) 278.5 nm (ε17700).

B. 9-(2-Hydroxyethyl)-$N^2$-phenylguanine [HE-PG].

a. 2-Anilino-6-chloropurine was reacted with 2-acetoxyethyl bromide as described above in A.a. 2-Anilino-6-chloro-9-(2-acetoxyethyl)purine was isolated in a 47% yield, mp 193°–194° C.

b. Hydrolysis of product a. by refluxing in 0.5N sodium hydroxide gave 9-(2-hydroxyethyl)-$N^2$-phenylguanine in a 73% yield, mp 338°–339° C. $^1H$ NMR δ10.52 (s, 1-H), 8.80 (s, 2-NH), 7.75 (s, 8-H), 7.35 (m, $C_6H_5$), 4.96 (t, 3'-OH), 4.08 (t, 1'-H), 3.96 (q, 2'-H). UV $\lambda_{max}$ ($H_2O$) 275.5 nm (ε16300), (1-octanol) 278.5 nm (ε19100).

C. 9-(2-Hydroxyethyl)-$N^2$-(m-[trifluoromethyl]phenyl)guanine.

a. 2-(m-[Trifluoromethyl]anilino)-6-chloro-9-(2-acetoxyethyl)purine was obtained from 2-(m-

[trifluoromethylanilino)-6-chloropurine and 2-acetoxyethyl bromide using the methods described in A.a. in a 19% yield after crystallization from DMF/chloroform. $^1$H NMR δ10.39 (s, 2-NH), 8.39 (s, 8-H), 7.84 (m, C$_6$H$_4$), 4.45 (t, 1'-CH$_2$), 3.33 (t, 2'-CH$_2$), 1.87 (s, CH$_3$).

b. Hydrolysis of the product of C.a. was performed as described in A.b., above, giving 9-(2-hydroxyethyl)-N$^2$-(m-[trifluoromethyl]phenyl)guanine in a 37% yield (from DMF/chloroform), mp 347°–349° C. $^1$H NMR δ11.12 (s, 1-H), 9.64 (s, 2-NH), 8.37 (s, 8-H), 7.57 (m, C$_6$H$_4$), 4.99 (t, 2'-OH), 4.09 (t, 1'-CH$_2$), 3.77 (q, 2'-CH$_2$). $^{19}$F NMR δ93.02 (s, CF3).

D. 9-(4-Hydroxybutyl)-N$^2$-phenylguanine [HB-PG].

a. Reaction between 2-anilino-6-chloropurine and 4-acetoxybutyl bromide was performed as described in A.a., above, giving 2-anilino-6-chloro-9-(4-acetoxybutyl) purine in a 45% yield (from DMF/chloroform), mp 195°–197° C. $^1$H NMR δ9.98 (s, 2-NH), 8.32 (s, 8-H), 7.31 (m, C$_6$H$_5$), 4.20 (t, 1'-CH$_2$), 4.02 (t, 4'-CH$_2$), 1.95 (s, CH$_3$), 1.92, 1.58 (m, 2'/3'CH$_2$).

b. Hydrolysis as described for A.b., above, gave 9-(4-hydroxybutyl)-N$^2$-phenylguanine in a 83% yield (from DMF/chloroform), mp>350° C. $^1$H NMR δ10.96 (s, 1-H), 9.46 (s, 2-NH), 7.86 (s, 8-H), 7.35 (m, C$_6$H$_5$), 4.46 (t, 4'-OH), 4.06 (t, 1'-CH$_2$), 3.42 (m, 4'-CH$_2$), 1.84,1.40 (m, 2'/3'-CH$_2$).

E. (N$^2$-Phenylguan-9-yl)acetic acid [PG-AA].

a. Reaction between 2-anilino-6-chloropurine and methyl bromoacetate as described for A.a. gave methyl (2-anilino-6-chloropurin-9-yl)acetate in 74% yield (from DMF/chloroform), mp 187°–188° C. $^1$H NMR δ10.02 (s, 2-NH), 8.28 (s, 8-H), 7.30 (m, C$_6$H$_5$), 5.14 (s, 1'-CH$_2$), 3.74 (s, CH$_3$).

b. Hydrolysis of the product of E.a. as described for A.b. gave (N$^2$-phenylguan-9-yl)acetic acid in 82% yield (from DMF/chloroform), mp 312°–315° C. $^1$H NMR δ11.11 (s, 1-H), 9.43 (s, 2-NH), 7.76 (s, 8-H), 7.30 (m, C$_6$H$_5$), 4.74 (s, 1'-CH$_2$).

EXAMPLE 2

Synthesis of N$^2$-alkylguanines.

A. N$^2$-(n-Dodecyl)guanine [C$_{12}$G].

A mixture of 2-bromohypoxanthine (0.5 g), n-dodecylamine (0.86 g) and n-dodecylamine hydrochloride (0.43 g) in 20% water:2-methoxyethanol (15 mL) was heated at reflux for 20 hours. After cooling, the precipitate was collected and crystallized from ethanol (with charcoal) to give 0.37 g (50%). Alternatively, 2-bromohypoxanthine (0.5 g) and n-dodecylamine (3 mL) were placed in a stainless steel pressure vessel and heated to 160° C. for 26 hours. Hot ethanol was added to the cooled mixture, and the solution was decolorized with charcoal. After chilling the crystallized product was collected by filtration and crystallized again from ethanol (with charcoal) to give the product in 40% yield. N$^2$-(n-Decyl)guanine and other N$^2$-alkylguanines are prepared similarly.

B. N$^2$-(n-propyl)-2$^1$deoxy guanosine [PrdG].

2-Bromo-2'-deoxyinosine (132 mg, 0.4 mmol) was suspended in ethanol (4 mL) and treated with n-propylamine (709 mg, 12 mmol). The suspension in a glass screw-top tube was placed in a steel bomb and heated at 120° C. for 18 hours. After cooling the solvent was evaporated and the residue was adsorbed to silica gel, and placed atop a silica gel column (2 g, 70–230 mesh) prepared in chloroform. After a wash with chloroform (100 mL), the product was eluted with 5% methanol in chloroform containing 0.1% triethylamine followed by 10% methanol in chloroform containing 0.1% triethylamine (800 mL). The solvent was removed, and the residue was crystallized from ethanol to give 44.7 mg (40%) of colorless crystals, mp 204°–204° C. UV and $^1$HNMR spectra and elemental analysis confirmed the structure.

Other 9-(2-deoxyribofuranosyl)-N$^2$-alkylguanines, e.g. EtdG, MedG, C$_{10}$dG, are made by exactly analogous methods.

C. 9-(2,3-Dihydroxypropyl), 9-(2-hydroxyethyl) and 9-(4-hydroxybutyl)-N$^2$-alkylguanines.

These compounds are made by methods exactly analogous to those described in Examples 1 A, B and D, respectively. Briefly, the sodium salt of the 2-alkylamino-6-chloropurine in acetonitrile is treated with epibromohydrin, 2-acetoxyethyl bromide or 4-acetoxybutyl bromide, respectively, and the major 9-substituted product is separated from the minor 7 substituted product. The 9-substituted product is heated at reflux in 0.5N sodium hydroxide for 2 hours. After neutralization with 0.5N hydrochloric acid, the precipitated products are crystallized from DMF/chloroform to give the title compounds.

D. 9-(2-Deoxyribofuranosyl)-N$^2$-phenylguanine [PhdG].

Synthetic method has been published: Focher et al. (1988) J. Med. Chem. 31:1496–1500.

EXAMPLE 3

Properties of 9-substituted-N$^2$-phenylguanines

Table 1, below recites the solubilities, partition coefficients, and concentrations at which 50% of either HSV1 or HSV2 thymidine kinase inhibition is observed for representative compounds of the invention.

TABLE 1

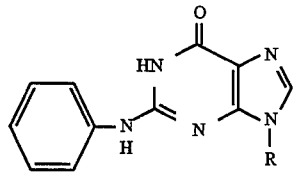

| R | (µM)$^1$ HSV1 TK | IC$_{50}$ HSV2 TK | Sol. in H$_2$O (µM) | Partition coeff. (oct: H$_2$O)$^2$ |
|---|---|---|---|---|
| H | 8 | 1.6 | 76.0– | 22.4 |
| —CH$_2$CH=CH$_2$ | 0.45 | 0.18 | 8.1– | 56.2 |

TABLE 1-continued

[Structure: phenyl-NH-C(=N)-NH-C(=O) fused imidazole with N-R substituent]

| R | (μM)[1] HSV1 TK | IC$_{50}$ HSV2 TK | Sol. in H$_2$O (μM) | Partition coeff. (oct: H$_2$O)[2] |
|---|---|---|---|---|
| HO-[furanose ring]-OH | 0.3 | 0.7 | 81.0 | 2.5 |
| —CH$_2$CHCH$_2$—S—CH$_2$CH$_2$OH<br>  OH | 1.6 | 1.56 | 29.8– | 6.7 |
| —CH$_2$CHCH$_2$—OH<br>  OH | 1.7 | 3.5 | 170.6+ | 2.5 |
| —CH$_2$CH$_2$OH | 2.9 | 1.2 | 156.3+ | 6.8 |
| —CH$_2$—O—CH(CH$_2$OH)$_2$ | 0.5 | tbd | 112.8+ | 1.0 |
| —CH$_2$CO$_2$H | 12.4 | 9.8 | tbd | tbd |
| —CH$_2$CH$_2$CH$_2$CH$_2$OH | 0.16 | 2.2 | 56.– | 18. |

[1]50% inhibitory concentrations [IC$_{50}$] against thymidine kinases (TK) from Herpes simplex virus types 1 and 2 (HSV1, HSV2).
[2]Ratio of concentrations of compound in 1-octanol and water at equilibrium. tbd - to be done.

EXAMPLE 4

Absorption and distribution of 9-substituted-N$^2$-phenylquanines in mice.

Tables 2 and 3 provide the results of two separate experiments demonstrating the superior half-life and distribution properties of several compounds of the invention (acronyms defined below) compared to a prototype base m-CF$_3$PG (N$^2$-(m-[trifluoromethyl]phenyl)guanine, and a nucleoside PhdG (N$^2$-phenyl-2'-deoxyguanosine).

Compound abreviations used herein:
DHP-PG: 9-(2,3-Dihydroxypropyl)-N$^2$-phenylguanine,
HE-PG: 9-(2-Hydroxyethyl)-N$^2$-phenylguanine,
HB-PG: 9-(4-Hydroxybutyl)-N$^2$-phenylguanine, and
PG-AA: (NE-phenylguan-9-yl)acetic acid,

TABLE 2

| Drug | Mode of administration* | Plasma half-life (min) | Volume of Distribution (L/Kg) |
|---|---|---|---|
| In saline, pH 11.3: | | | |
| m-CF$_3$PG | i.v. | 25 | 3.0 |
|  | i.p. | 140 | ** |
| PhdG | i.v. | 7.5 | 0.4 |
|  | i.p. | 60 | ** |
| In 90% DMSO/H$_2$O: | | | |
| HE-PG | i.v. | 15 | 3.3 |
|  | i.p. | 19 | 4.3 |
| PG-AA | i.p. | 33 | 1.7 |
| HB-PG | i.p. | 85 | 12.7 |
| In corn oil: | | | |
| HB-PG | i.p. | 55 | † |

*i.v., intravenous; i.p., intraperitoneal.
**Absorption slow and incomplete.
†slow absorption

TABLE 3

Pharmacokinetic parameters of inhibitors in mice following intraperitoneal (100 mg/Kg) administration (i.p.)

| Acronym | Vehicle | Plasma t$_{1/2}$[1] (min) | C$_0$(μM)[2] |
|---|---|---|---|
| mCF$_3$PG | saline, pH 11.4 | 140 | 10.2 |
| PhdG | saline, pH 11.4 | 60 | 11.7 |
| HB-PG | 90% DMSO | 75 | 30.5 |
| DHP-PG | 90% DMSO | 17.3 | 115 |
| HE-PG | 90% DMSO | 21 | 100 |
| PG-AA | 90% DMSO | 26.6 | 246 |

[1]Plasma concentrations were measured by analytical HPLC on a C8 reverse phase column as described in the experimental Section.
[2]Plasma concentration extrapolated to t = 0.

Figure 2:
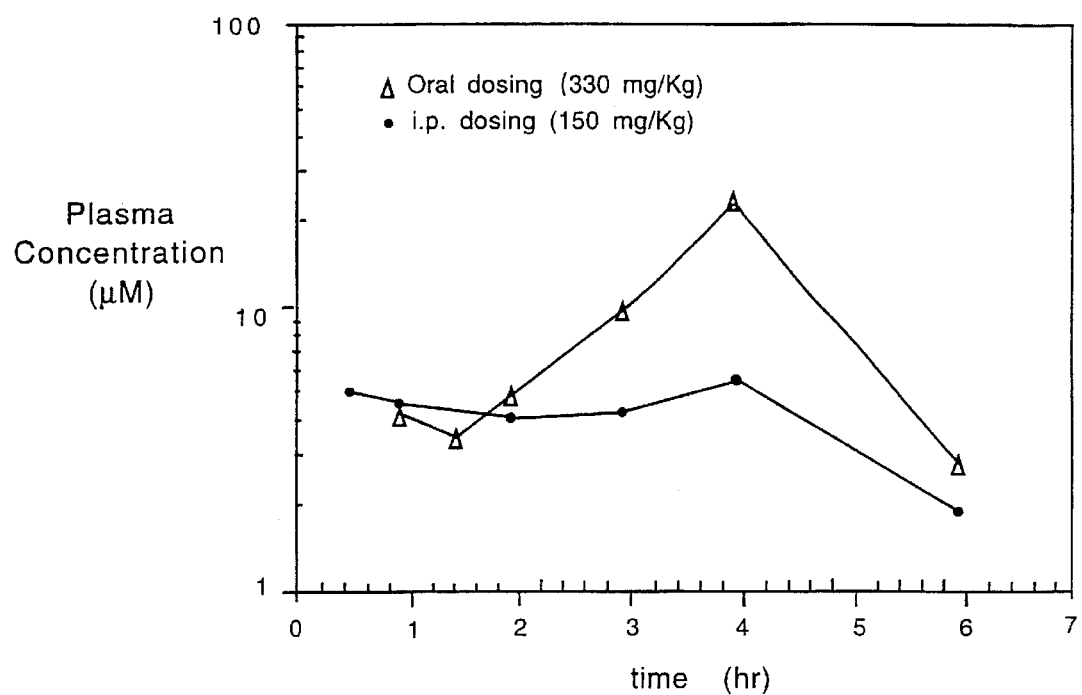
Figure 3:
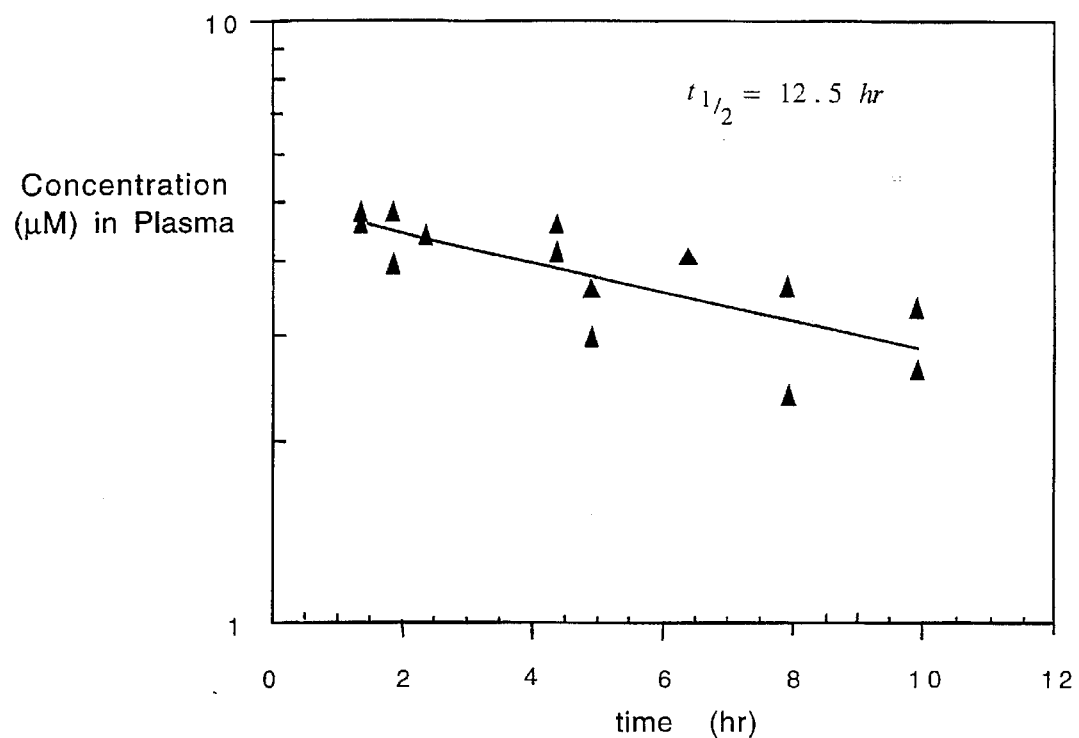
Figure 4:
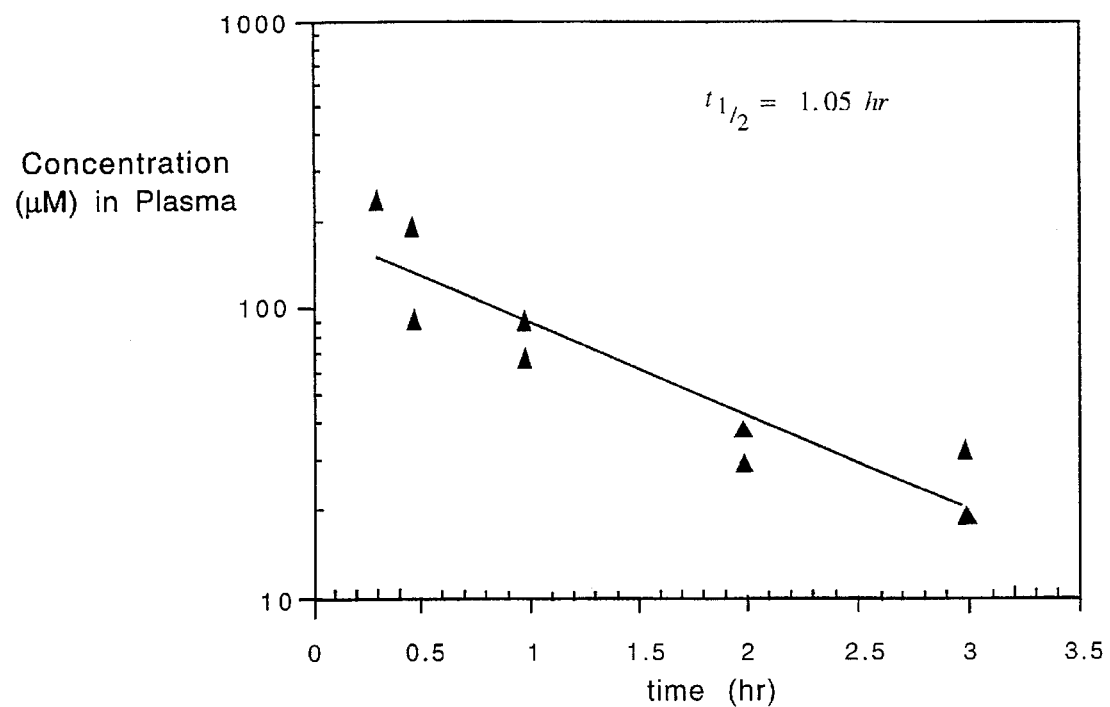

FIGS. 1–4 show the plasma concentration time curves for HB-PG. FIG. 1 shows the time course for interperitoneal (i.p.) and intravenous (i.v.) administration of HP-BG in 90% DMSO, 33% DMSO, and corn oil. FIG. 2 shows the time course for HB-PG when administered in a corn oil suspension by i.v. and i.p. injection to rabbits. FIG. 3 shows the time course for plasma concentration of HB-PG when administered to squirrel monkeys when administered by i.p. injection. FIG. 4 shows the time course for HB-PG administration to squirrel monkeys when administered by i.v. injection.

EXAMPLE 5

The effect of HB-PG on hypothermia-induced HSV1 reactivation in mice.

Tables 4 and 5 show the effect of HBPG on hyperthermia-induced HSV1 reactivation in mice. Table 4 is a quantitation of reactivated virus levels using measurement of infectious virus levels. Table 5 provides quantitation of viral DNA using quantitative, competitive polymerase chain reaction methods.

TABLE 4

Effect of HBPG* on Hyperthermia-Induced Viral Reactivation‡

| Treatment | No. Mice | Infectious VirusΔ | |
|---|---|---|---|
| | | Ganglion | Ocular Surface |
| HBPG, stressed | 10 | 7/18 | 3/20 |
| Placebo, stressed | 10 | 12/19 | 8/17 |
| HBPG, not stressed | 5 | 0/8 | 0/9 |
| Placebo, not stressed | 5 | 0/10 | 0/10 |

*HBPG = $N^2$-phenyl-9-(4-hydroxybutyl) guanine.
‡HSV-1 latent mice were treated with HBPG (200 mg/kg), stressed by immersion in 43° C. water for 10 min, and sacrificed 24 hours later.
ΔGanglion homogenates and ocular surface swabs were co-cultured on indicator cells and the appearance of cytopathic effect recorded.
There is statistically significant difference between the frequency of virus in the samples from the HBPG-treated animals compared to the placebo-treated animals, $P < 0.05$.

TABLE 5

Effect of HBPG* on Hyperthermia-Induced Viral DNA Synthesis‡

| Treatment | Viral DNAΔ |
|---|---|
| HBPG, stressed | $<1 \times 10^2$ copies |
| Placebo, stressed | $1 \times 10^4$ copies |

*HBPG = $N^2$-phenyl-9-(4-hydroxybutyl) guanine.
‡HSV-1 latent mice were treated with HBPG (200 mg/kg), stressed by immersion in 43° C. water for 10 min, and sacrificed 24 hours later
ΔGanglionic DNA was amplified in quantitative, competitive polymerase chain reaction (QC-PCR) and the copy number of the viral gene present determined at the equivalence point.

EXAMPLE 6

Effect of HSV TK inhibitors on reactivation in vitro.

Table 6 shows the effect of the compounds of the invention in reducing the reactivation of latent HSV (KOS and McKrae) infection on the mouse ganglia.

TABLE 6

Effect of HSV TK Inhibitors on Reactivation In Vitro (# ganglia reactivated/# explanted)

| Cpd | HSV1, strain KOS[1] | HSV1, strain McKrae[2] |
|---|---|---|
| [Control] | 11/18 | 3/4 |
| PhdG | 3/20 | 1/4 |
| MCF₃PG | 1/20 | 0/4 |
| HE-PG | | 4/4 |
| HB-PG | | 2/4 |
| DHP-PG | | 4/4 |
| PGAA | | 4/4 |

Latent ocular HSV1 infections were established in mice. Trigeminal ganglia were removed and treated as follows.
[1]Ganglia were minced and cocultivated on Vero cells in the presence of 150 μM drugs (from Leib et al., Antimicr. Agents Chemother. 34, 1285 (1990)).
[2]Ganglia were minced and incubated for 7 days in the presence of 150 μM drugs; after homogenization, supernatant was added to Vero cells in culture (courtesy of Dr. Y. J. Gordon, Eye and Ear Institute, Pittsburgh).

EXAMPLE 8

Characteristics of VZV TK inhibitors

Table 7 shows the inhibitory effect which the compounds of the invention have on VZV Thymidine Kinase.

TABLE 7

Inhibitors of Varicella Zoster Virus (VZV) Thymidine Kinase (TK)

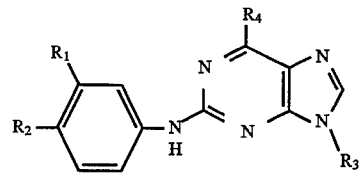

| Acronym | $R_1$ | $R_2$ | $IC_{50}$ (μM)[1] |
|---|---|---|---|
| C₈G | n-C₈H₁₇ | H | 48+ |
| C₁₀G | n-C₁₀H₂₁ | H | 21~ |
| C₁₂G | n-C₁₂H₂₅ | H | 4.3[2]~ |
| C₁₄G | n-C₁₄H₂₉ | H | 69+ |
| EtdG | CH₂CH₃ | 2-deoxyribofuranosyl | 48+ |
| PRdg | n-C₃H₇ | " | 20[3]~ |
| PHdG | C₆H₅ | " | 9.4~ |
| HBPG | " | 4-hydroxybutyl | 40+ |

[1]Concentration causing 50% inhibition of 0.4 μM [³H]thymidine phosphorylation catalyzed by VZV TK.
[2]Competitive inhibitor, $K_i = 3.2$ μM.
[3]Competitive inhibitor, $K_i = 13.6$ μM.

The examples provided above are meant to illustrate the synthesis and characterization of a representative subset of the compounds of the invention. Analogous methods known to one skilled in the art can be used for the synthesis and characterization of other compounds of the invention (see, for example, "Advanced Organic Chemistry," J. March, 3rd. ed., New York: John Wiley, 1985; "The Chemistry of Functional Groups," S. Patai, Ed., New York: John Wiley, multiple volumes, 1960ff; Heterocyclic and nucleoside synthesis—"Purines," J. H. Lister, New York: Wiley-Interscience, 1971; "Chemistry of Nucleosides and Nucleotides," Vols 1 and 2, L. B. Townsend, Ed., New York: Plenum Press, 1988; Medicinal chemistry—"The Basis of Medicinal Chemistry," 4th ed., 3 vols., M. E. Wolff, Ed., New York: Wiley-Interscience, 1980, all incorporated herein by reference).

Other embodiments are within the following claims.

What is claimed is:

1. A 9-substituted-$N^2$-phenylguanine of the formula wherein each $R_1$ and $R_2$, independently,=H, a hydrophobic and electron-attracting group, or CH₂CH₃;

$R_3$=CH₂CH(OH)CH₂OH, (CH₂)ₙOH (where n is 2-5), (CH₂)ₙCOOH, (where n is 1-4), CH₂CH(OH)CH₂OCOR₅, (CH₂)ₙOCOR₅ (where n is 2-5), or (CH₂)ₙCOOR₅ (where n is 1-4);

$R_5$=CH₃, CH₂CH₃, CH₂CH₂NH₂, CH₂CH₂N(C₂H₅)₂, or CH₂CH₂CO₂H; and $R_4$=OH, H, Cl, or NH₂;

or a pharmaceutically acceptable salt thereof.

2. The compound of claim 1, wherein each $R_1$ and $R_2$, independently,=H, CH₂CH₃, X, CX₃, CX₂CX₃, CH₂CX₃, CHX₂, or OCX₃ (where X=a halogen);

$R_3$=CH$_2$CH(OH)CH$_2$OH; and
$R_4$=OH.

3. The compound of claim 1, wherein each of $R_1$ and $R_2$, independently,=H, CH$_2$CH$_3$, X, CX$_3$, CX$_2$CX$_3$, CH$_2$CX$_3$, CHX$_2$, or OCX$_3$ (where X=a halogen);

$R_3$=(CH$_2$)$_n$OH (where n is 2–5); and $R_4$=OH.

4. The compound of claim 1, wherein each $R_1$ and $R_2$, independently,=H, CH$_2$CH$_3$, X, CX$_3$, CX$_2$CX$_3$, CH$_2$CX$_3$ CHX$_2$, or OCX$_3$ (where X=a halogen);

$R_3$=(CH$_2$)$_n$COOH (where n is 1–4); and $R_4$=OH.

5. The compound of claim 1, wherein each $R_1$ and $R_2$, independently,=H, CH$_2$CH$_3$, X, CX$_3$, CX$_2$CX$_3$, CH$_2$CX$_3$, CHX$_2$, or OCX$_3$ (where X=a halogen);

$R_3$=CH$_2$CH(OH)CH$_2$—O—COR$_5$, (CH$_2$)$_n$OCOR$_5$, (where n is 2–5) and R$_5$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H; and $R_4$=OH.

6. The compound of claim 1, wherein each $R_1$ and $R_2$, independently,=H, CH$_2$CH$_3$, X, CX$_3$, CX$_2$CX$_3$, CH$_2$CX$_3$, CHX$_2$, or OCX$_3$ (where X=a halogen);

$R_3$=(CH$_2$)$_n$COOR$_5$ (where n is 1–4) and $R_5$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H; and $R_4$=OH.

7. The compound of claim 1, wherein $R_4$=H, Cl, or NH$_2$.

8. An N$^2$-phenylguanine of the formula:

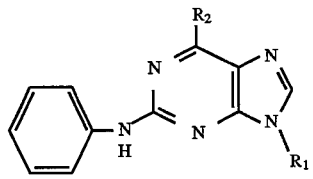

wherein $R_1$=2-deoxyribofuranosyl, (CH$_2$)$_n$OH (where n is 2–5), CH$_2$CH(OH)CH$_2$OH, (CH$_2$)$_n$—COOH (where n is 1–4).;

CH$_2$CH(OH)CH$_2$—O—COR$_3$, (CH$_2$)$_n$—O—COR$_3$ (where n is 2–5), or (CH$_2$)$_n$CO—OR$_3$ (where n is 1–4), wherein R$_3$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H; and $R_2$=H or Cl, or a pharmaceutically acceptable salt thereof.

9. The compound of claim 8, wherein $R_1$=2-deoxyribofuranosyl, —(CH$_2$)$_n$OH (where n is 2–5), or CH$_2$CH(OH)CH$_2$OH.

10. The compound of claim 8, wherein $R_1$=(CH$_2$)$_n$—COOH (where n is 1–4).

11. The compound of claim 8, wherein $R_1$=CH$_2$CHOHCH$_2$—O—COR$_3$ or (CH$_2$)$_n$—O—COR$_3$ (where n is 2–5) and R$_3$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H.

12. The compound of claim 8, wherein $R_1$=(CH$_2$)$_n$CO—OR$_3$ (where n=1–4) and $R_3$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H.

13. An N$^2$-alkylguanine of the formula:

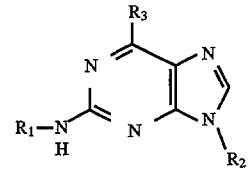

wherein $R_1$=normal or branched chain C$_n$H$_{2n+1}$ (where n is 1–12);

$R_2$=H, 2-deoxyribofuranosyl, (CH$_2$)$_n$OH (where n is 2–5), CH$_2$CH(OH)CH$_2$OH, (CH$_2$)$_n$—COOH (where n is 14), CH$_2$CH(OH)CH$_2$—O—COR$_4$, (CH$_2$)$_n$—O—COR$_4$ (where n is 2–5), or (CH$_2$)$_n$CO—OR$_4$ (where n is 1–4);

$R_4$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H; and $R_3$=OH, H, Cl, or NH$_2$;

or a pharmaceutically acceptable salt thereof.

14. The compound of claim 13, wherein $R_1$=normal or branched chain C$_n$H$_{2n+1}$ (where n is 1–12);

$R_2$=H; and $R_3$=OH.

15. The compound of claim 13, wherein $R_1$=normal or branched chain C$_n$H$_{2n+1}$ (where n=1–12), $R_2$=2-deoxyribofuranosyl, —(CH$_2$)$_n$OH (where n=2–5), or CH$_2$CH(OH)CH$_2$OH; and $R_3$=OH.

16. The compound of claim 13, wherein $R_1$=normal or branched chain C$_n$H$_{2n+1}$ (where n=1–12);

$R_2$=(CH$_2$)$_n$—COOH (where n=1–4); and $R_3$=OH.

17. The compound of claim 13, wherein $R_1$=normal or branched chain C$_n$H$_{2n+1}$ (where n=1–12), $R_2$=CH$_2$CH(OH)CH$_2$—O—COR$_4$, (CH$_2$)$_n$—O—COR$_4$ (where n=2–5);

$R_3$=OH; and $R_4$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H.

18. The compound of claim 13, wherein $R_1$=normal or branched chain C$_n$H$_{2n+1}$ (where n=1–12);

$R_2$=(CH$_2$)$_n$CO—OR$_4$ (where n=1–4);

$R_3$=OH; and $R_4$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H.

19. The compound of claim 13, wherein $R_1$=normal or branched chain C$_n$H$_{2n+1}$ (where n=1–12);

$R_2$=(CH$_2$)$_n$CO—OR$_4$ (where n=1–4);

$R_3$=H, Cl, or NH$_2$; and $R_4$=CH$_3$, CH$_2$CH$_3$, CH$_2$CH$_2$NH$_2$, CH$_2$CH$_2$N(C$_2$H$_5$)$_2$, or CH$_2$CH$_2$CO$_2$H.

20. A method of treating a patient with a latent herpes virus infection, said method comprising administering a compound of claim 1, 8, or 13 to said patient.

21. The method of claim 19, wherein said herpes virus is herpes simplex virus 1.

22. A method of treating a patient with a latent herpes virus infection, said method comprising administering 9-(2-deoxyribofuranosyl)-N$^2$-phenylguanine to said patient.

23. A method of treating a patient with a herpes simplex virus 1 infection, said method comprising administering a compound of claim 1 to said patient.

24. The method of claim 22, wherein said herpes virus is herpes simplex virus 1.

25. The method of claim 19, wherein said herpes virus is herpes simplex virus 2.

26. A method of treating a patient with a herpes simplex virus 2 infection, said method comprising administering a compound of claim 1 to said patient.

27. The method of claim 22, wherein said herpes virus is herpes simplex virus 2.

28. The method of claim 19, wherein said herpes virus is Varicella-Zoser virus.

29. A method of treating a patient with a Varicella-Zoster virus infection, said method comprising administering a compound of claim 8 or 13 to said patient.

30. The compound of claim 1, 8, or 13 in a pharmaceutically acceptable carrier.

* * * * *

UNITED STATES PATENT AND TRADEMARK OFFICE
CERTIFICATE OF CORRECTION

PATENT NO. : 5,646,155
DATED : July 8, 1997
INVENTOR(S) : George E. Wright

It is certified that error appears in the above-identified patent and that said Letters Patent is hereby corrected as shown below:

Column 1, line 7 insert:

--<u>Government Support</u>

Work described herein was supported by one or more grants from the U.S. Government. The U.S. Government has certain rights in the invention.--

Signed and Sealed this

Thirteenth Day of June, 2000

*Attest:*

Q. TODD DICKINSON

*Attesting Officer*     *Director of Patents and Trademarks*